US009446980B2

(12) United States Patent
Campbell, Jr.

(10) Patent No.: US 9,446,980 B2
(45) Date of Patent: *Sep. 20, 2016

(54) CERAMIC GLAZE HAVING ANTIMICROBIAL PROPERTY

(71) Applicant: MICROBAN PRODUCTS COMPANY, Huntersville, NC (US)

(72) Inventor: Alvin Lamar Campbell, Jr., Huntersville, NC (US)

(73) Assignee: Microban Products Company, Huntersville, NC (US)

( * ) Notice: Subject to any disclaimer, the term of this patent is extended or adjusted under 35 U.S.C. 154(b) by 0 days.
This patent is subject to a terminal disclaimer.

(21) Appl. No.: 13/931,805

(22) Filed: Jun. 28, 2013

(65) Prior Publication Data

US 2015/0030863 A1    Jan. 29, 2015

Related U.S. Application Data

(62) Division of application No. 12/032,657, filed on Feb. 16, 2008, now abandoned.

(51) Int. Cl.

| *B32B 18/00* | (2006.01) |
| *C03C 8/00* | (2006.01) |
| *C03C 8/20* | (2006.01) |
| *C04B 33/34* | (2006.01) |
| *C04B 41/86* | (2006.01) |
| *C04B 41/00* | (2006.01) |
| *C04B 41/50* | (2006.01) |
| *A01N 59/16* | (2006.01) |
| *A01N 25/08* | (2006.01) |
| *A01N 25/34* | (2006.01) |
| *C03C 8/14* | (2006.01) |
| *A01N 59/20* | (2006.01) |
| *C04B 41/91* | (2006.01) |
| *A01N 59/02* | (2006.01) |
| *A61K 33/24* | (2006.01) |
| *A61K 33/30* | (2006.01) |
| *A61K 33/38* | (2006.01) |

(52) U.S. Cl.
CPC .................. *C03C 8/20* (2013.01); *A01N 25/08* (2013.01); *A01N 25/34* (2013.01); *A01N 59/02* (2013.01); *A01N 59/16* (2013.01); *A01N 59/20* (2013.01); *A61K 33/245* (2013.01); *A61K 33/30* (2013.01); *A61K 33/38* (2013.01); *C03C 8/14* (2013.01); *C04B 33/34* (2013.01); *C04B 41/009* (2013.01); *C04B 41/0072* (2013.01); *C04B 41/505* (2013.01); *C04B 41/5022* (2013.01); *C04B 41/5027* (2013.01); *C04B 41/5041* (2013.01); *C04B 41/5049* (2013.01); *C04B 41/86* (2013.01); *C04B 41/91* (2013.01); *C03C 2204/02* (2013.01); *C03C 2209/00* (2013.01)

(58) Field of Classification Search
CPC .............. B32B 15/00; B32B 2255/00; B32B 2255/20; B32B 2313/00; B32B 2315/00; B32B 2315/02; B32B 18/00; B32B 2250/02; B32B 2307/754; C03C 1/00; C03C 8/00; C03C 8/14; C03C 8/22; C03C 2204/00; C03C 2204/02; C03C 2203/50; C03C 2203/52; C03C 2205/04; C03C 17/00; C03C 17/22; C03C 17/23

USPC ....... 428/409, 426, 428, 432, 688, 689, 697, 428/699, 701, 702; 501/14, 21, 41
See application file for complete search history.

(56) References Cited

U.S. PATENT DOCUMENTS

| 5,304,516 | A | | 4/1994 | Clifford |
| 5,807,641 | A | * | 9/1998 | Oku .......................... C03C 8/14 428/428 |
| 5,853,866 | A | * | 12/1998 | Watanabe et al. .......... 428/312.8 |
| 5,882,808 | A | | 3/1999 | Oku et al. |
| 6,043,171 | A | | 3/2000 | Siebers et al. |
| 6,303,183 | B1 | * | 10/2001 | Wilczynski et al. .......... 427/193 |
| 6,368,668 | B1 | | 4/2002 | Kobayashi et al. |
| 6,383,646 | B1 | | 5/2002 | Tomioka et al. |
| 6,514,622 | B1 | * | 2/2003 | Hayakawa et al. ........... 428/432 |
| 6,756,060 | B1 | * | 6/2004 | Greenspan et al. .......... 424/489 |
| 6,887,812 | B2 | | 5/2005 | Nenasheva et al. |
| 7,250,178 | B2 | | 7/2007 | Olsson et al. |
| 7,476,698 | B2 | * | 1/2009 | Wagener et al. ............. 523/122 |
| 7,488,442 | B2 | * | 2/2009 | Matsumoto et al. ......... 264/602 |
| 2003/0134107 | A1 | * | 7/2003 | Machida ............... C04B 41/009 428/336 |
| 2004/0103823 | A1 | | 6/2004 | Kurihara et al. |

(Continued)

FOREIGN PATENT DOCUMENTS

| CA | 2 279 785 A1 | 2/2000 |
| CN | 1615698 A | 5/2005 |

(Continued)

OTHER PUBLICATIONS

CN 1843995 English Human translation. Dec. 2012.*
Enamel (9th Edition of Encyclopedia Britannica—free ninth edition online encyclopedia Britannica >> vol. 8 [ELE-FAK].*
Supplementary Partial European Search Report for corresponding European Application EP 08730070, mailed May 15, 2015, all enclosed pages cited.
Supplementary European Search Report for corresponding European Application EP 08730070, mailed Oct. 5, 2015, all enclosed pages cited.
PCT/US2008/054190, Form PCT/ISA/210 (International Search Report) (3 pages, dated Jun. 30, 2008).
PCT/US2008/054190, Form PCT/ISA/237 (Written Opinion) (4 pages, dated Jun. 30, 2008).
AATCC Committee RA31, "AATCC Test Method 100-1999, Antibacterial Finishes on Textile Materials: Assesment of", AATCC Technical Manual/2003, pp. 149-151.
Ernest M. Levin, Carl R. Robbins and Howard F. McMurdie, "Phase Diagrams for Ceramists", Compiled at the National Bureau of Standards, Copyright 1964 by The American Ceramic Society, pp. 69 and 120, published in Columbus, Ohio.
Herbert V. Oliveira et al., "Manual of Drying and Firing Porcelain Enamel", PEI-601, Version 1.2, published by the Porcelain Enamel Institute, Nashville, Tennessee, copyright 1996-1997, pp. 1-22.

(Continued)

*Primary Examiner* — Lauren R Colgan
(74) *Attorney, Agent, or Firm* — Nelson Mullins Riley & Scarborough LLP

(57) ABSTRACT

An antimicrobial ceramic glazing composition contains one or more antimicrobial agents disposed therein. Methods for making and using the glazing composition are disclosed, as well as substrates having a fired antimicrobial glaze thereon. The antimicrobial agents comprise metallic oxides, with a subset of the disclosed combinations exhibiting synergistic effect in fired glazes.

13 Claims, No Drawings

(56) References Cited

U.S. PATENT DOCUMENTS

| | | | |
|---|---|---|---|
| 2005/0035500 A1* | 2/2005 | Matsumoto et al. | 264/602 |
| 2005/0106336 A1* | 5/2005 | Ong | C04B 28/02 428/15 |
| 2005/0158400 A1* | 7/2005 | Olsson et al. | 424/641 |
| 2005/0196430 A1* | 9/2005 | Olsson et al. | 424/443 |
| 2005/0252410 A1 | 11/2005 | Bujard et al. | |
| 2006/0048676 A1 | 3/2006 | Bujard | |
| 2007/0110824 A1 | 5/2007 | Nageswaran | |
| 2007/0275168 A1 | 11/2007 | Prochazka | |
| 2009/0104459 A1* | 4/2009 | Campbell, Jr. | 428/446 |
| 2009/0117173 A1 | 5/2009 | Chen et al. | |
| 2012/0237686 A1 | 9/2012 | Chen et al. | |

FOREIGN PATENT DOCUMENTS

| | | | |
|---|---|---|---|
| CN | 1843995 | * | 10/2006 |
| DE | 198 34 801 A1 | | 2/2002 |
| DE | 20 2005 006 784 U1 | | 9/2005 |
| JP | H111380 A | | 1/1999 |
| WO | 0014029 A1 | | 3/2000 |

OTHER PUBLICATIONS

Japanese Minister of International Trade and Industry and the Japanese Industrial Standards Committee, "Antimicrobial products—Test for antimicrobial activity and efficacy", Standardiztion Journal translated and published by the Japanese Standards Association, Reference No. JIS Z 2801 : 2000(E), published Dec. 20, 2000, Tokyo, Japan, pp. 1-11.

Richard A. Eppler with Mimi Obstler, "Understanding Glazes", published by The American Ceramic Society, Westerville, Ohio, 2005, pp. 246, 247, 315.

ASTM International Designation: C286, "Standard Terminology Relating to Porcelain Enamel and Ceramic-Metal Systems", copyright ASTM International 1999 (Reapproved 2009) published Jan. 2010, West Conhohocken, PA, pp. 1 and 4.

The Edward Orton Jr. Ceramic Foundation, "Temperature Equivalent Chart for Orton Pyrometric Cones ( C)", www.ortonceramic.com, 2011.

ASTM International Designation: C 347-57 (Reapproved 1983), "Standard Test Method for Reflectance, Reflectivity, and Coefficient of Scatter of White Porcelain Enamels", copyright ASTM International International, Annual Book of Standards, vol. 14.02, published Dec. 1983, pp. 733-735.

PCT International Search Report and Written Opinion; PCT/US2015/064634, mailed Feb. 16, 2016; all enclosed pages cited.

* cited by examiner

CERAMIC GLAZE HAVING ANTIMICROBIAL PROPERTY

CROSS-REFERENCE TO RELATED APPLICATIONS

This application claims priority to U.S. Ser. No. 60/890,666 and U.S. Ser. No. 60/890,673, each filed on Feb. 20, 2007, the contents of which are incorporated by reference as though fully set forth herein.

FIELD OF THE INVENTION

The present invention relates to the field of antimicrobial protection in a ceramic article or component thereof. More specifically, the present invention relates to a composition for imparting built-in and long lasting antimicrobial characteristics to ceramic products.

BACKGROUND OF THE INVENTION

An area of particular commercial interest in the art is ceramic articles and ceramic coatings. Ceramic coatings are commonly used in products that store, treat, or transport water and liquid waste. Ceramic toilets, urinals, bidets, bathroom basins (collectively known as sanitary ware), flooring tiles and other bathroom fixtures are probably the most common example of such products.

When used to collect, contain and/or transport water, ceramic products often become stained by scum and films of biologic origin (e.g., bacteria, fungus, mold, mildew). To date, the primary method of removing biological scum and film from these ceramic products has been to abrade the ceramic surface in the presence of a topical cleaning agent.

There is a need for a ceramic coating that has built-in protection against the growth and proliferation of microbes. However, existing technologies are somewhat limited in this regard. For example, the high temperatures used in ceramic firing processes typically preclude the use of organic antimicrobial agents.

Conventional inorganic silver-based antibacterial compounds (e.g., zeolite, amorphous glass, sol-gel) generally are too expensive for commercial use. Moreover, incorporation of silver-based antimicrobial agents into ceramic glazes routinely presents issues of clouding, crazing, discoloration, and other undesirable consequences to the glaze aesthetics.

Zinc oxide is known as having antimicrobial characteristics and has been used in the preparation of ceramic glazing compositions. However, known ceramic glazing compositions that rely solely upon zinc oxide as an antimicrobial agent have not shown antimicrobial efficacy sufficient for control of microbial growth and proliferation on ceramic surfaces.

Accordingly, there is a need for a low-cost ceramic coating that offers persistent built-in antimicrobial protection.

DETAILED DESCRIPTION

As used herein, the terms "microbe" or "microbial" should be interpreted to refer to any of the microscopic organisms studied by microbiologists or found in the use environment of a ceramic article or ceramic-glazed article. Such organisms include, but are not limited to, bacteria and fungi as well as other single-celled organisms such as mold, mildew and algae. Viral particles and other infectious agents are also included in the term microbe.

As well, "antimicrobial" and like terms should be interpreted as encompassing both microbe-killing as well as microbistatic activities. That is, it herein is considered efficacious if an antimicrobial composition reduces the number of microbes on a substrate or it the composition retards the normal rate of microbial growth.

For ease of discussion, this description uses the terms microbes and antimicrobial to denote a broad spectrum activity (e.g. against bacteria and fungi). When speaking of efficacy against a particular microorganism or taxonomic rank, the more focused term will be used (e.g. antifungal to denote efficacy against fungal growth in particular).

Using the above example, it should be understood that efficacy against fungi does not in any way preclude the possibility that the same antimicrobial composition demonstrates efficacy against another class.

For example, discussion of the strong bacterial efficacy demonstrated by a disclosed embodiment should not be read to exclude the embodiment from also demonstrating antifungal activity. This method of presentation should not be interpreted as limiting the scope of the invention in any way.

A first embodiment is an antimicrobial ceramic glaze composition. A second embodiment disclosed herein is a method for making an antimicrobial ceramic glazing composition. The glaze composition comprises a plurality of conventional glaze ingredients and a combination of antimicrobial agents, as described more fully below.

The following brief discussion of ceramic coatings and in particular to ceramic glazing on the outer surfaces of ceramic products and of vitreous china or ceramic production is provided as an aid to the reader. This discussion is presented in the context of the production of bathroom fixtures. Those skilled in the art recognize that the production process of ceramic products may vary from that which is presented below, and that the ceramic glazing process disclosed herein is adaptable to other substrates.

Glazes are generally made from powdered glass combined with colored oxides of such elements as cobalt, chrome, manganese, or nickel. The powder mixture is suspended in water and applied to the ceramic surface by spraying, brushing, dipping, or other known application methods.

The suspension, or slip, in which the glaze is applied to the ceramic surface must have particular properties to ensure that the glaze is easy to apply, does not run during firing, and adheres well both when wet and after firing. These slip properties are often obtained by adding a small amount of clay to the suspension and by controlling both the amount of water in the slip as well as the size of the powder particles. Organic surface-active agents (e.g. surfactants, detergents) also can be added to the slip to improve its properties.

Colors in glazes are controlled by adding coloring agents to the glassy components of the glaze. Special effects in glazes can also be produced. If salt is added to the kiln during firing, the glaze develops a fine orange-peel texture, which can be uniform or spotty depending upon conditions. A glaze that froths during firing gives a rough surface of broken bubbles known as a blister glaze.

It was undertaken to develop a baseline glaze composition—that is, a conventional, non-antimicrobial ceramic glaze base—and methodology to aid in identification of suitable and efficacious antimicrobial agents. By way of specific technical background, development of the baseline glaze, its processing, and its maturing temperature are now briefly reviewed.

Two potential glaze frits were identified that did not contain any of the antimicrobial agents that could comprise at least 95% of the glaze composition. These frits were used to constitute glaze slips that were applied to bisque-fired tile. The slips were evaluated at different solids contents and viscosities. It is also preferable that the glazes be easy to apply by multiple methods.

A conventional glaze composition used for experimental trials herein is composed of 95% slow-fire base glaze (containing primarily $SiO_2$ and secondarily, inter alia, KNaO, CaO, BaO, SrO $Al_2O_3$ and $B_2O_3$).

Alkaline earth oxide materials such as calcium carbonate, wollastonite, and zinc oxide are generally added as raw materials. Other alkaline earth oxides such as lead oxide, strontium oxide, barium oxide, and magnesium oxide are more typically added in a fritted form. The alkaline earth oxides are advantageous because they provide fluxing action without having a major effect on glaze thermal expansion. Oxides also can serve as coloring compounds.

Also resident in the glaze composition is 5% EPK kaolin, and an over-addition of 1% Bentonite (an absorbent aluminum silicate clay formed from volcanic ash and well known to those of skill in the ceramic art). This dry material is blended into a sufficient quantity of de-ionized water to produce a glaze slip with a specific gravity of 1.35±0.05 g/cc. This represents a solids content of 41.74%.

Notable among the many antimicrobial agents used were $Ag_2CO_3$ (CAS No. 534-16-7); $Bi_2O_3$ (CAS No. 1304-76-3); CuO (CAS No. 1317-38-0); $SnO_2$ (CAS No. 18282-10-5); $TiO_2$ (anatase; CAS No. 13463-67-7); and ZnO (CAS No. 1314-13-2).

An antimicrobial glazing composition was made by adding together (e.g. by mixing) conventional glazing composition components and antimicrobial agent combinations. The components and antimicrobial agent(s) were added based on weight of the solids content of the baseline glaze, excluding such antimicrobial agent(s). The glaze base is described in greater detail above.

The glaze base, with antimicrobial agent(s) admixed therein, then was ball milled for fifteen minutes. The milled glaze base was held overnight to allow for hydration, then remixed. The antimicrobial glazing composition then was ready to be applied to a substrate (e.g. a bisque tile).

All material addition calculations are based upon the percent solids of the baseline glaze and the specific gravity is checked before each group of material evaluation samples is processed. Each material to be evaluated is added to 1000 milliliters of baseline glaze.

It is expected, however, that other conventional ceramic glaze compositions could be substituted without departing from the essential features of the antimicrobial ceramic glaze as described herein.

In a third embodiment, a method of affixing a ceramic glaze to a substrate confers durable antimicrobial properties to the substrate. The method generally comprises providing a ceramic glazing composition having one or more antimicrobial agents disposed therein as set forth in the present disclosure, applying the antimicrobial glazing composition to a substrate, and curing the glazing composition in accordance with conventional glaze-firing techniques.

Development work utilized dipping to apply the glaze formulation to tiles, although other methods of application known to those in the art may be used. The glaze is then dried and fixed onto the ceramic surface by firing.

During firing, the powdered glass softens and largely equilibrates over the ceramic surface, reacting with the ceramic substrate to form a strong, adherent union therewith. If a glaze is applied to an already fired ceramic substrate, a second firing is necessary to melt and bond the glaze to the substrate. Alternatively, it is possible to apply a glaze to an unfired ceramic and fire both the glaze and substrate together.

Various components, such as alkali oxide, borates, and lead oxide can be added to the ceramic glaze composition to facilitate softening at lower temperatures in order that the glaze flow more easily during firing and to minimize roughness and defects in the fired ceramic glaze surface. The present antimicrobial combinations are compatible with these common additives.

The initial stage of a typical ceramic production process is the production of barbotine or slip, a clay from which bathroom ceramic products are made. Barbotine is made from a mixture of clays, kaolin, phyllites, feldspar and quartz.

Individual pieces are cast by pouring the barbotine into molds made of gypsum or microporous resin. In the casting processes that use gypsum molds, the parts are formed by absorption of water contained in the barbotine through the capillary action of the gypsum. As water leaves the barbotine the part solidifies to a point where the mold can be opened. The still malleable part is then removed from the mold.

Casting processes that use resin molds are called "high pressure" processes. Parts are formed by filtering water contained in the barbotine clay through micropores in the resin molds by the application of pressure. The water is eliminated by injecting compressed air along the molds.

After casting and removal from the molds, the parts go for drying in kilns under controlled humidity and temperature (approximately 90.degree. C.). The drying cycle lasts about 7 hours, reducing the water content of the part from about 16% to less than 1%. Following this, the parts are inspected to detect possible flaws. The parts then go to the coating process. The coating process is alternatively referred to as the glazing step.

The glazing step typically comprises the application of ceramic glaze on the parts using guns in individual booths fitted with exhaust systems and water curtains. Typical ceramic glaze is produced from a mixture of kaolin, feldspar, quartz, colorings and other additives. Once coated, the parts are fired in continuous kilns, reaching temperatures of about 1250° C. in an approximately 15-hour cycle. The firing process gives the glazed part the color and transparent appearance that is typical of vitreous china.

The procedure to manufacture material evaluation samples is straightforward. A reservoir of baseline glaze, as described above, is maintained. Sample tiles have applied thereon or thereto the present glaze composition; the present disclosure relates to dipped sample tiles.

Each dipped tile was placed into a tile sagger, each sagger capable of holding up to twenty tiles. The sagger was placed into one of the two electric kilns and fired to a Pyrometric Cone Equivalent of 06. This measure of thermal history is roughly equivalent to 1889° F. or 1062° C. Baseline glaze samples were fired at temperatures ranging from 1888° F. to 2194° F.

The above procedure approximates a glaze application in a production environment. The final baseline glaze formulations resulted in samples having a glassy surface at a low temperature, highly resistant to absorption of dyes, and exhibiting no antimicrobial properties.

Microscopic imaging of the baseline glaze/tile interface revealed complete vitrification of the glaze with no inclusions of bubbles or unmelted materials. The baseline samples are the foundation for comparing and judging the candidate materials. The adopted baseline glaze is simple in composition, easy to process and apply, and has a low firing temperature. These attributes greatly facilitated the evaluation of candidate material samples.

In production, this dried glaze layer is about 2 millimeters in thickness. A more cost efficient method of producing an antimicrobial surface would entail use of a much thinner secondary glaze applied over the regular (first) glaze. This glaze thickness could be 0.5 millimeters or less in thickness.

It is expected that exposure of the glazed tile to microbes will result in microbial contact only with the glazed composition on the surface of the glazed tile. Material below the surface is trapped within the glass of the glaze and thereby sequestered from microbes.

A variety of antimicrobial agents were tested in the baseline glaze composition after glazing of a substrate sample. Of these compounds, a variety of combinations also were assessed, as detailed in the following discussion and examples In a fourth embodiment, a ceramic article bearing the above-described antimicrobial glaze composition exhibits durable antimicrobial properties. The antimicrobial ceramic article comprises a substrate, for example a ceramic substrate, having at least a first surface; and a fired or cured glaze disposed on at least a portion of the first surface. The ceramic glazing composition utilized in this embodiment is the same as that described in the first embodiment.

Antimicrobial agents were used to manufacture a range of antimicrobial glaze compositions, each composition consisting of one, two or three antimicrobial agents. Several ceramic articles then were prepared to test the antimicrobial characteristics of the recited glazes. The test articles comprised an underlying ceramic substrate made from a standard commercial barbotine.

The glaze used in the testing was the baseline glaze described previously, to which was added varying quantities of antimicrobial agent combinations as noted. The glaze composition was applied to the articles by dipping, and the test articles were then fired.

As mentioned, combinations of two antimicrobial agents were assessed for antimicrobial efficacy in fired glazes on ceramic substrates. The compounds $Ag_2CO_3$, $Bi_2O_3$, CuO, $SnO_2$, $TiO_2$, and ZnO were evaluated. Each compound was sequentially trialed at 2% in tandem with one of the other five compounds. The second compound was trialed at either 2% or 4%. As an example using $Ag_2CO_3$ and ZnO, then, the following possibilities were tested: 2% $Ag_2CO_3$ and 2% ZnO; 2% $Ag_2CO_3$ and 4% ZnO; and 4% $Ag_2CO_3$ and 2% ZnO.

Continuing with this exemplary combination of antimicrobial agents, the combination of 4% $Ag_2CO_3$ and 4% ZnO was not tested, as 4%/4% combinations generally are considered too expensive to be commercialized and/or are have been observed to negatively affect the aesthetics of the glaze finish. It is expected that such combinations would show efficacy if the 2%/4% and/or 4%/2% combination was efficacious, although antagonistic effects have been observed for some combinations.

Test articles also were prepared without any antimicrobial agents in the glaze for use as a negative control.

The measure of antimicrobial efficacy is the reduction in the number of organisms surviving the testing protocol in comparison with the baseline standard. Minimum efficacy is assumed to originate at a reduction level of 1 common logarithm (log (NOS Std/NOS Sample)).

Three samples of each addition level and three baseline glaze samples were then tested in triplicate. The testing is in accordance with a modified JIS Z2801:2000 test protocol (available from Japanese Industrial Standards Committee, Tokyo, Japan). The Z2801 protocol is an internationally known standard test for antimicrobial activity and efficacy. The protocol and specific modifications made thereto are summarized below.

Sample tile pieces having a diameter of approximately 55 mm were used. Ceramic glaze composition was applied and fired according to the instructions for the commercial glaze base employed. This preparation process yielded test disks having about a top surface area of about 2500 square millimeters.

The comparison test for antimicrobial efficacy used *Klebsiella pneumoniae*, ATCC 4352. The test organism was grown, and a portion of an exponentially growing culture was collected into Japanese Nutrient Broth (JNB) diluted 1/500. An inoculum was prepared at about $10^6$ colony-forming units (CFU) per milliliter by dilution with 1/500 JNB.

A sample tile was placed on moistened laboratory tissue in a culture plate, and 75 microliters of test inoculum (~$0.8 \times 10^5$ CFU) was pipetted onto the sample surface. A cover slip or film was placed over and in contact with the inoculum to ensure uniform and substantially complete coverage of the inoculum over the sample surface. The culture plate then was incubated for 24 hours at 37° with humidity.

Bacteria on the sample and cover slip/film were recovered, collected into D/E Neutralizing Broth, and counted. The antimicrobial activity of the test samples is expressed herein as a log reduction value, as compared to the bacterial growth of the corresponding untreated (control) sample. A log reduction is expressed as $\log(U/B)$, where U is the average CFU of the test organism from the inoculum recovered in the Neutralizing Broth from the negative control (untreated) sample tile, and B is the average CFU of the test organism recovered in the Neutralizing Broth from the inoculated sample.

EXAMPLE 1

In a first example, 2% $Ag_2CO_3$ was utilized as a first antimicrobial agent in a family of glaze compositions, which further contained a second antimicrobial agent: one of $Bi_2O_3$, CuO, $SnO_2$, $TiO_2$ or ZnO. The second antimicrobial agent was tested at both 2% and 4%. Sample tiles were glazed and the tiles were evaluated according to the above-described modified JIS Z2801:2000 test protocol for the effect of the glazed tile on bacterial reduction. Results are shown in TABLE 1.

EXAMPLE 2

In a second example, 2% $Bi_2O_3$ was utilized as a first antimicrobial agent in a family of glaze compositions, which further contained a second antimicrobial agent: one of $Ag_2CO_3$, CuO, $SnO_2$, $TiO_2$ or ZnO. The second antimicrobial agent was tested at both 2% and 4%. Sample tiles were glazed and the tiles were evaluated according to the above-described modified JIS Z2801:2000 test protocol for the effect of the glazed tile on bacterial reduction. Results are shown in TABLE 2.

TABLE 1

| Antimicrobial Combination: $Ag_2CO_3$ | | | | | | K. Pneumoniae |
|---|---|---|---|---|---|---|
| $Ag_2CO_3$ | $Bi_2O_3$ | CuO | $SnO_2$ | $TiO_2$ | ZnO | Log reduction |
| — | — | — | — | — | — | NA |
| 2% | — | — | — | — | — | 2.4 |

TABLE 1-continued

| Antimicrobial Combination: Ag$_2$CO$_3$ | | | | | | K. Pneumoniae |
|---|---|---|---|---|---|---|
| Ag$_2$CO$_3$ | Bi$_2$O$_3$ | CuO | SnO$_2$ | TiO$_2$ | ZnO | Log reduction |
| 2% | 2% | — | — | — | — | 3.6 |
| 2% | 4% | — | — | — | — | 3.0 |
| 2% | — | 2% | — | — | — | 3.9 |
| 2% | — | 4% | — | — | — | 3.8 |
| 2% | — | — | 2% | — | — | 3.2 |
| 2% | — | — | 4% | — | — | 1.9 |
| 2% | — | — | — | 2% | — | 2.4 |
| 2% | — | — | — | 4% | — | 2.7 |
| 2% | — | — | — | — | 2% | 3.0 |
| 2% | — | — | — | — | 4% | 3.3 |

EXAMPLE 3

In a third example, 2% CuO was utilized as a first antimicrobial agent in a family of glaze compositions, which further contained a second antimicrobial agent: one of Ag$_2$CO$_3$, Bi$_2$O$_3$, SnO$_2$, TiO$_2$ or ZnO. The second antimicrobial agent was tested at both 2% and 4%. Sample tiles were glazed and the tiles were evaluated according to the above-described modified JIS Z2801:2000 test protocol for the effect of the glazed tile on bacterial reduction. Results are shown in TABLE 3.

TABLE 2

| Antimicrobial Combination: Bi$_2$O$_3$ | | | | | | K. Pneumoniae |
|---|---|---|---|---|---|---|
| Bi$_2$O$_3$ | Ag$_2$CO$_3$ | CuO | SnO$_2$ | TiO$_2$ | ZnO | Log reduction |
| — | — | — | — | — | — | NA |
| 2% | — | — | — | — | — | 0.8 |
| 2% | 2% | — | — | — | — | 1.3 |
| 2% | 4% | — | — | — | — | 3.7 |
| 2% | — | 2% | — | — | — | 1.9 |
| 2% | — | 4% | — | — | — | 3.1 |
| 2% | — | — | 2% | — | — | 0.5 |
| 2% | — | — | 4% | — | — | 0.9 |
| 2% | — | — | — | 2% | — | −0.2 |
| 2% | — | — | — | 4% | — | 0.8 |
| 2% | — | — | — | — | 2% | 0.7 |
| 2% | — | — | — | — | 4% | 1.4 |

TABLE 3

| Antimicrobial Combination: CuO | | | | | | K. Pneumoniae |
|---|---|---|---|---|---|---|
| CuO | Ag$_2$CO$_3$ | Bi$_2$O$_3$ | SnO$_2$ | TiO$_2$ | ZnO | Log reduction |
| — | — | — | — | — | — | NA |
| 2% | — | — | — | — | — | 0.4 |
| 2% | 2% | — | — | — | — | 3.8 |
| 2% | 4% | — | — | — | — | 4.0 |
| 2% | — | 2% | — | — | — | 2.5 |
| 2% | — | 4% | — | — | — | 1.9 |
| 2% | — | — | 2% | — | — | 0.3 |
| 2% | — | — | 4% | — | — | 2.4 |
| 2% | — | — | — | 2% | — | 2.0 |
| 2% | — | — | — | 4% | — | 2.3 |
| 2% | — | — | — | — | 2% | 0.5 |
| 2% | — | — | — | — | 4% | 3.0 |

EXAMPLE 4

In a fourth example, 2% SnO$_2$ was utilized as a first antimicrobial agent in a family of glaze compositions, which further contained a second antimicrobial agent: one of Ag$_2$CO$_3$, Bi$_2$O$_3$, CuO, TiO$_2$ or ZnO. The second antimicrobial agent was tested at both 2% and 4%. Sample tiles were glazed and the tiles were evaluated according to the above-described modified JIS Z2801:2000 test protocol for the effect of the glazed tile on bacterial reduction. Results are shown in TABLE 4.

TABLE 4

| Antimicrobial Combination: SnO$_2$ | | | | | | K. Pneumoniae |
|---|---|---|---|---|---|---|
| SnO$_2$ | Ag$_2$CO$_3$ | Bi$_2$O$_3$ | CuO | TiO$_2$ | ZnO | Log reduction |
| — | — | — | — | — | — | NA |
| 2% | — | — | — | — | — | 0.1 |
| 2% | 2% | — | — | — | — | 0.5 |
| 2% | 4% | — | — | — | — | 3.7 |
| 2% | — | 2% | — | — | — | 1.2 |
| 2% | — | 4% | — | — | — | 0.5 |
| 2% | — | — | 2% | — | — | 0.5 |
| 2% | — | — | 4% | — | — | 4.0 |
| 2% | — | — | — | 2% | — | 0.0 |
| 2% | — | — | — | 4% | — | 0.1 |
| 2% | — | — | — | — | 2% | 0.2 |
| 2% | — | — | — | — | 4% | 0.4 |

TABLE 5

| Antimicrobial Combination: TiO$_2$ | | | | | | K. Pneumoniae |
|---|---|---|---|---|---|---|
| TiO$_2$ | Ag$_2$CO$_3$ | Bi$_2$O$_3$ | CuO | SnO$_2$ | ZnO | Log reduction |
| — | — | — | — | — | — | NA |
| 2% | — | — | — | — | — | 0.0 |
| 2% | 2% | — | — | — | — | 0.8 |
| 2% | 4% | — | — | — | — | 3.6 |
| 2% | — | 2% | — | — | — | 0.7 |
| 2% | — | 4% | — | — | — | 0.7 |
| 2% | — | — | 2% | — | — | 0.4 |
| 2% | — | — | 4% | — | — | 3.9 |
| 2% | — | — | — | 2% | — | 0.0 |
| 2% | — | — | — | 4% | — | 0.5 |
| 2% | — | — | — | — | 2% | 0.0 |
| 2% | — | — | — | — | 4% | 0.2 |

EXAMPLE 5

In a fifth example, 2% TiO$_2$ was utilized as a first antimicrobial agent in a family of glaze compositions, which further contained a second antimicrobial agent: one of Ag$_2$CO$_3$, Bi$_2$O$_3$, CuO, SnO$_2$ or ZnO. The second antimicrobial agent was tested at both 2% and 4%. Sample tiles were glazed and the tiles were evaluated according to the above-described modified JIS Z2801:2000 test protocol for the effect of the glazed tile on bacterial reduction. Results are shown in TABLE 5.

EXAMPLE 6

In a sixth example, 2% ZnO was utilized as a first antimicrobial agent in a family of glaze compositions, which further contained a second antimicrobial agent: one of Ag$_2$CO$_3$, Bi$_2$O$_3$, CuO, SnO$_2$ or TiO$_2$. The second antimicrobial agent was tested at both 2% and 4%. Sample tiles were glazed and the tiles were evaluated according to the above-described modified JIS Z2801:2000 test protocol for the effect of the glazed tile on bacterial reduction. Results are shown in TABLE 6.

TABLE 6

Antimicrobial Combination: ZnO — K. Pneumoniae

| ZnO | $Ag_2CO_3$ | $Bi_2O_3$ | CuO | $SnO_2$ | $TiO_2$ | Log Reduction |
|---|---|---|---|---|---|---|
| — | — | — | — | — | — | NA |
| 2% | — | — | — | — | — | 0.4 |
| 2% | 2% | — | — | — | — | 2.4 |
| 2% | 4% | — | — | — | — | 3.7 |
| 2% | — | 2% | — | — | — | 1.3 |
| 2% | — | 4% | — | — | — | 1.5 |
| 2% | — | — | 2% | — | — | 0.5 |
| 2% | — | — | 4% | — | — | 3.7 |
| 2% | — | — | — | 2% | — | 0.2 |
| 2% | — | — | — | 4% | — | 0.2 |
| 2% | — | — | — | — | 2% | −0.1 |
| 2% | — | — | — | — | 4% | 0.1 |

TABLE 7

Antimicrobial Combination: $Ag_2CO_3$ — K. Pneumoniae

| $Ag_2CO_3$ | $Bi_2O_3$ | CuO | $SnO_2$ | $TiO_2$ | ZnO | Log reduction |
|---|---|---|---|---|---|---|
| — | — | — | — | — | — | NA |
| 2% | — | — | — | — | — | 2.4 |
| — | 2% | — | — | — | — | 0.8 |
| 2% | 2% | — | — | — | — | 3.6 |
| 2% | 4% | — | — | — | — | 3.0 |
| 2% | — | — | — | — | — | 2.4 |
| — | — | 2% | — | — | — | 0.4 |
| 2% | — | 2% | — | — | — | 3.9 |
| 2% | — | 4% | — | — | — | 3.8 |
| 2% | — | — | — | — | — | 2.4 |
| — | — | — | 2% | — | — | 0.1 |
| 2% | — | — | 2% | — | — | 3.2 |
| 2% | — | — | 4% | — | — | 1.9 |
| 2% | — | — | — | — | — | 2.4 |
| — | — | — | — | 2% | — | 0.0 |
| 2% | — | — | — | 2% | — | 2.4 |
| 2% | — | — | — | 4% | — | 2.7 |
| 2% | — | — | — | — | — | 2.4 |
| — | — | — | — | — | 2% | 0.4 |
| 2% | — | — | — | — | 2% | 3.0 |
| 2% | — | — | — | — | 4% | 3.3 |

RESULTS

When two chemical antimicrobial agents are used in combination, either in a single composition or as two separate additions at the point of use, three results are possible: 1) an additive (neutral) effect; 2) an antagonistic effect; or 3) a synergistic effect.

An additive (neutral) effect has no economic advantage over the individual antimicrobial agents. An antagonistic effect would produce a negative or reduced-efficacy result.

Only synergism, which is much less likely than an additive or an antagonistic effect, gives a positive result and, therefore possesses economic advantages.

According to the invention, the combinations identified below demonstrate an unexpected and synergistic antimicrobial effect in a fired ceramic glaze. The combinations of first and second antimicrobial agents, as described herein, achieve superior antimicrobial activity at lower antimicrobial agent concentrations as compared to the antimicrobial capability of either antimicrobial agent alone. Such a superior effect presents a distinct economic advantage and increases the effectiveness of the antimicrobial combination per unit weight.

Looking at the results for antimicrobial agents singly and in combinations where the first antimicrobial agent is 2% $Ag_2CO_3$ (results in TABLE 7), it can be seen that a 2% addition of one antimicrobial agent alone demonstrated a range of efficacy results: $Ag_2CO_3$ (2.4; efficacy), $Bi_2O_3$ (0.8; weak efficacy), CuO (0.4; very weak efficacy), ZnO (0.4; very weak efficacy), $SnO_2$ (0.1; essentially no efficacy) and $TiO_2$ (0.0; no efficacy).

However, it readily can be seen that simple additions of a second antimicrobial agent at 2% resulted in any one of additive, antagonistic, or synergistic effect. Moreover, addition of the second antimicrobial agent at 4% did not generate results in keeping with expectations based on the test results of individual antimicrobial agents or [2%+2%] antimicrobial agent combinations.

For combinations of $Ag_2CO_3$ and $Bi_2O_3$, the [2% $Ag_2CO_3$+2% $Bi_2O_3$] combination exhibits a synergistic effect relative to the results to be expected.

However, it is noted that twice the level of the second antimicrobial agent (that is, [2% $Ag_2CO_3$+4% $Bi_2O_3$]) displays an antagonistic effect, wherein the observed efficacy is lower than both (a) the expected additive log reduction value for [2% $Ag_2CO_3$+4% $Bi_2O_3$]; and (b) the observed log reduction value for the [2% $Ag_2CO_3$+2% $Bi_2O_3$] combination.

For combinations of $Ag_2CO_3$ and CuO, the [2% $Ag_2CO_3$+ 2% CuO] combination exhibits a strong synergistic effect relative to the expected results based on merely additive principles. Increasing the level of the second antimicrobial agents two-fold (that is, [2% $Ag_2CO_3$+4% CuO]) destroys the synergistic effect, instead resulting in antagonism: the observed efficacy of the [2% $Ag_2CO_3$+4% CuO] combination (3.8) is essentially the same as the [2% $Ag_2CO_3$+2% CuO] combination (3.9/3.8) and well below the very high expected log reduction for this combination.

$Ag_2CO_3$ and $SnO_2$ demonstrated surprising and strong synergy for the [2% $Ag_2CO_3$+2% $SnO_2$] combination (3.2 log reduction). Unexpectedly, the combination of $Ag_2CO_3$ and $SnO_2$ showed marked antagonism when the $SnO_2$ concentration was doubled to 4%: log reduction tumbled to 1.9, well below both the observed result of 3.2 for the [2% $Ag_2CO_3$+2% $SnO_2$] combination as well as the expected additive result.

The results for 2% $Ag_2CO_3$ and 2% $TiO_2$ were concluded to be merely additive. Unexpectedly, though, doubling the $TiO_2$ to 4% resulted in a minor synergistic effect: the efficacy of the [2% $Ag_2CO_3$+4% $TiO_2$] combination (2.7 log reduction value) was slightly above both the expected additive-effect value for the combination and the observed log reduction for the [2% $Ag_2CO_3$+2% $TiO_2$] combination.

The assessment of $Ag_2CO_3$+ZnO combinations showed marginal synergy for the [2% $Ag_2CO_3$+4% ZnO] combination (3.0 observed log reduction value). The synergy was lessened with the increase in the ZnO concentration to 4% (3.3 actual).

The data presented for the other two-compound antimicrobial combinations likewise can be analyzed, and further examples identified of additive, synergistic, and antagonistic effect.

A number of combinations were deemed to be of special interest. These combinations are listed in TABLE 8 as showing synergistic effects. That is, the observed log reduction values of the combinations exceeded by a statistically significant margin the expected log reduction values based on the performance of the individual antimicrobial agent components of each combination.

In addition to the above binary combinations, a less expansive set of tertiary combinations were evaluated.

These combinations comprise $Bi_2O_3$, ZnO and $Ag_2CO_3$. Concentrations of the individual compounds in the tertiary combinations trialed include $Bi_2O_3$ at 1% and 2%; at ZnO at 1% and 2%; and $Ag_2CO_3$ at 0.5%, 1% and 2%.

TABLE 8

| Antimicrobial Combination | | | | | | Log |
|---|---|---|---|---|---|---|
| $Ag_2CO_3$ | $Bi_2O_3$ | CuO | $SnO_2$ | $TiO_2$ | ZnO | Reduction |
| 2% | — | 2% | — | — | — | 3.9 |
| 2% | — | — | 2% | — | — | 3.2 |
| 2% | — | — | — | — | 2% | 3.0 |
| 2% | — | — | — | 4% | — | 3.3 |
| 4% | — | 2% | — | — | — | 4.0 |
| 4% | — | — | 2% | — | — | 3.7 |
| 4% | — | — | — | 2% | — | 3.6 |
| 4% | — | — | — | — | 2% | 3.7 |
| — | 2% | 2% | — | — | — | 1.9 |
| — | 2% | 2% | — | — | — | 2.5 |
| — | 2% | 4% | — | — | — | 3.1 |
| — | — | 2% | 4% | — | — | 2.4 |
| — | — | 2% | — | 2% | — | 2.0 |
| — | — | 2% | — | 4% | — | 2.3 |
| — | — | 2% | — | — | 4% | 3.0 |
| — | — | 4% | 2% | — | — | 4.0 |
| — | — | 4% | — | 2% | — | 3.9 |
| — | — | 4% | — | — | 2% | 3.7 |
| 2% | 2% | — | — | — | — | 3.6 |
| 2% | 4% | — | — | — | — | 3.0 |
| 2% | — | 4% | — | — | — | 3.8 |
| 4% | 2% | — | — | — | — | 3.7 |

Initially, the three compounds were employed at equal concentrations of 1% and 2%. As well, combinations were assessed wherein one of $Bi_2O_3$, $Ag_2CO_3$ and ZnO was added at 2%, while the other two compounds were added at 1%. Lastly, trials were undertaken in which two compounds were added at 2% and the remaining compound at 1%. Results are collected into TABLE 9, with log reduction again expressed against bacterial growth on the untreated sample.

The tertiary combination data show that the three components were efficacious when present in the ceramic glaze composition at equal concentrations of 1%. Tertiary antimicrobial agent combinations in which an increase to 2% of one or both of the $Bi_2O_3$ concentration and the ZnO concentration likewise demonstrated efficacy against the bacterial inoculum.

Antimicrobial activity was greatest for the tertiary combination containing 2% each of $Bi_2O_3$, $Ag_2CO_3$ and ZnO. The strength of the antimicrobial activity for this combination exceeds that expected based on the performance of the component antimicrobial agents individually.

It should be noted that expectations of activity of binary and tertiary combinations are not reached by simply summing the log reduction values for the separate compounds at the relevant concentrations. Such an approach may be accurate in cases where the various component compounds share a common mechanism of action against the test organism.

TABLE 9

| Antimicrobial Agent | | | Log |
|---|---|---|---|
| $Bi_2O_3$ | ZnO | $Ag_2CO_2$ | Reduction |
| — | — | — | NA |
| 2% | — | — | 0.8 |
| — | 2% | — | 0.4 |
| — | — | 2% | 2.4 |
| 2% | 2% | — | 0.7 |
| 2% | — | 2% | 1.3 |

TABLE 9-continued

| Antimicrobial Agent | | | Log |
|---|---|---|---|
| $Bi_2O_3$ | ZnO | $Ag_2CO_2$ | Reduction |
| 2% | — | 4% | 3.7 |
| — | 2% | 2% | 3.0 |
| — | 2% | 4% | 3.7 |
| 1% | 1% | 1% | 2.9 |
| 2% | 1% | 1% | 2.4 |
| 1% | 2% | 1% | 2.3 |
| 1% | 1% | 2% | — |
| 2% | 2% | 1% | 1.8 |
| 2% | 1% | 2% | — |
| 1% | 2% | 2% | — |
| 2% | 2% | 2% | 3.5 |

However, the literature suggests that bismuth, zinc and silver do not behave identically in their mechanisms of bacterial attack. Without wishing to be bound by theory, in the present instance, zinc is believed to exert its effect by disruption of bacterial respiration and the delicate equilibrium of metals in the bacterial cell; bismuth is described as inhibiting the bacteria's ability to take up iron; and silver is believed to act on bacterial proteins involved in nucleic acid replication.

The results demonstrate that the ceramic glaze disclosed herein showed commercially acceptable efficacy against *Klebsiella pneumoniae* relative to the control. These results are exciting as permitting use of materials in considerably lower amounts than heretofore have been employed, especially for those compounds which have previously been explored as antimicrobial agents.

The observed results further indicate synergistic actions between materials, providing enhanced efficacy levels at lower addition amounts of the antimicrobial agents. Decreased addition amounts reduce the cost and potential deleterious effect of the compounds in the ceramic glaze.

As well, additional benefits are realized to the environment, in terms of both waste production during manufacture and disposal of the ceramic glaze articles upon termination of their useful product lives.

As noted previously, the antimicrobial ceramic glaze was designed to impart durable (persistent) and built-in antimicrobial protection to a variety of ceramic articles. Accordingly, the scope of the disclosure includes ceramic articles that incorporate the present antimicrobial glazing. Such articles include, but are not limited to, toilets, bidets, washbasins, towel rails, soap holders, toilet roll holders, water control fixtures (e.g., hot and cold water handles), and ceramic glazed tiles.

It will therefore be readily understood by those persons skilled in the art that the present composition and methods are susceptible of broad utility and application. Many embodiments and adaptations other than those herein described, as well as many variations, modifications and equivalent arrangements, will be apparent from or reasonably suggested to one of ordinary skill by the present disclosure and the foregoing description thereof, without departing from the substance or scope thereof.

Accordingly, while the present composition and methods have been described herein in detail in relation to its preferred embodiment, it is to be understood that this disclosure is only illustrative and exemplary and is made merely for purposes of providing a full and enabling disclosure.

The foregoing disclosure is not intended or to be construed to limit or otherwise to exclude any such other embodiments, adaptations, variations, modifications and equivalent arrangements.

What is claimed is:

1. An antimicrobial ceramic glazing composition, comprising:
   a ceramic glaze base adapted to be fired at a firing temperature of from at least about 1062° C.; and
   an antimicrobial composition including: a first antimicrobial agent consisting of $Ag_2CO_3$; and
   a second antimicrobial agent that is one of $Bi_2O_3$, CuO or ZnO;
   wherein the first antimicrobial agent is present in the glaze composition at a concentration of about 0.5 to about four percent, by weight of glaze composition; and
   wherein the second antimicrobial agent is present in the glaze composition at a concentration of from about one percent to about four percent, by weight of glaze composition; and
   wherein the glazing composition is adapted to possess an antimicrobial property after a conventional firing process at the firing temperature.

2. The antimicrobial ceramic glazing composition of claim 1 wherein the second antimicrobial agent is $Bi_2O_3$.

3. The antimicrobial ceramic glazing composition of claim 1 wherein the second antimicrobial agent is ZnO.

4. The antimicrobial ceramic glazing composition of claim 1 wherein the first antimicrobial agent and the second antimicrobial agent are present in the glaze composition at substantially equal concentrations.

5. The antimicrobial ceramic glazing composition of claim 1 wherein the concentration of the first antimicrobial agent in the glaze composition is about two percent;
   wherein the second antimicrobial agent is one of $Bi_2O_3$, CuO or ZnO.

6. The antimicrobial ceramic glazing composition of claim 1 wherein the concentration of the first antimicrobial agent in the glaze composition is about four percent; and wherein the second antimicrobial agent is present in the glaze composition at a concentration of about two percent.

7. The antimicrobial ceramic glazing composition of claim 1 wherein the second antimicrobial agent is CuO.

8. A glazed ceramic substrate, comprising:
   a ceramic substrate having a first substrate surface; and
   a fired antimicrobial ceramic glazing composition disposed on the first substrate surface;
   wherein the fired antimicrobial ceramic glazing composition is a post-fired state of an antimicrobial ceramic glazing composition including:
   a first antimicrobial agent consisting of $Ag_2CO_3$; and
   a second antimicrobial agent that is one of $Bi_2O_3$, CuO or ZnO;
   wherein the first antimicrobial agent is present in the glaze composition at a concentration of about 0.5 to about four percent, by weight of glaze composition; and
   wherein the second antimicrobial agent is present in the glaze composition at a concentration of from about one percent to about four percent, by weight of glaze composition.

9. The glazed ceramic substrate of claim 8 wherein the second antimicrobial agent is $Bi_2O_3$.

10. The glazed ceramic substrate of claim 8 wherein the second antimicrobial agent is CuO.

11. The glazed ceramic substrate of claim 8 wherein the second antimicrobial agent is ZnO.

12. The glazed ceramic substrate of claim 8 wherein the concentration of the first antimicrobial agent is about two percent and the second antimicrobial agent is one of $Bi_2O_3$, CuO or ZnO.

13. The glazed ceramic substrate of claim 8 wherein the concentration of the first antimicrobial agent is about four percent and the second antimicrobial agent is one of $Bi_2O_3$, CuO or ZnO.

* * * * *